United States Patent [19]
Kobayashi et al.

[11] Patent Number: 5,546,181
[45] Date of Patent: Aug. 13, 1996

[54] OPTICAL DETECTOR EMPLOYING AN OPTICALLY-ADDRESSED SPATIAL LIGHT MODULATOR

[75] Inventors: Yuji Kobayashi; Narihiro Yoshida; Naohisa Mukohzaka; Haruyoshi Toyoda; Tsutomu Hara, all of Hamamatsu, Japan

[73] Assignee: Hamamatsu Photonics K.K., Shizuoka-ken, Japan

[21] Appl. No.: 316,478

[22] Filed: Oct. 3, 1994

[30] Foreign Application Priority Data

Oct. 1, 1993 [JP] Japan .................................. 5-246902

[51] Int. Cl.⁶ .............................. G01N 21/00; G02B 27/42
[52] U.S. Cl. ............................................ 356/237; 250/550
[58] Field of Search .................................. 356/237, 239, 356/394, 392; 250/550, 572, 562; 382/8, 31; 359/561, 560, 559, 564, 568

[56] References Cited

U.S. PATENT DOCUMENTS

| | | | |
|---|---|---|---|
| 4,806,774 | 2/1989 | Lin et al. | 356/237 |
| 5,172,000 | 12/1992 | Scheff et al. | 356/237 |
| 5,289,260 | 2/1994 | Miyazaki et al. | 356/237 |
| 5,379,150 | 1/1995 | Miyazaki et al. | 356/237 |

FOREIGN PATENT DOCUMENTS

| | | |
|---|---|---|
| 2114154 | 4/1990 | Japan . |
| 545862 | 2/1993 | Japan . |

OTHER PUBLICATIONS

"Optical Inspection of Industrial Pattern Defect Using New Spatial Filter" (Journal of the Electrotechnical Research, 43–7,8), 1979.

"Optical Inspection of Manufactured Glass Using Adaptive Fourier Filtering" (Optical Engineering), vol. 27 No. 5, May 1988, pp. 358–364.

"Real–Time Enhancement of Defects in a Periodic Mask Using Photorefractive $Bi_{12}SiO_{20}$" (Optics Letters), vol. 10 No. 9, Sep. 1985, pp. 430–432.

"Real–Time Defect Inspection of Periodic Patterns Using Self–Pumped Barium Titanate Crystal" (Optics Communications), vol. 77 No. 2,3, Jun. 15, 1990, pp. 135–138.

*Variable Nonlinear Transfer Characteristics of MSLM*, Kobayashi et al., Japanese Journal of Applied Physics, vol. 29, No. 8. Aug., 1990, pp. L1529–L1532.

*Primary Examiner*—Hoa Q. Pham
*Attorney, Agent, or Firm*—Sughrue, Mion, Zinn, Macpeak & Seas

[57] ABSTRACT

In an optical detector, a light source irradiates coherent light onto an objective. A Fourier transform lens receives the light diffracted and scattered at the objective and Fourier transforms the light to generate a Fourier image, the Fourier image having a high intensity spectral component corresponding to the periodic pattern on the objective and a low intensity spectral component corresponding to the abnormal portion. In an optically-addressed spatial light modulator, each of the optically-addressing part and the light modulating part receives the Fourier image at the corresponding portions. A threshold driving controller controls the spatial light modulator in its threshold operation so as to change a state in the light modulating part at a region where the high intensity spectral component of the Fourier image is incident while preventing the state from being changed in the light modulating part at a region where the low intensity spectral component of the Fourier image is incident, the changed state in the light modulating part modulating the high intensity spectral component of the Fourier image incident in the light modulating part. Thus, the modulated high intensity spectral component is separated from the unmodulated low intensity spectral component.

9 Claims, 10 Drawing Sheets

5,546,181

OPTICAL DETECTOR EMPLOYING AN OPTICALLY-ADDRESSED SPATIAL LIGHT MODULATOR

BACKGROUND OF THE INVENTION

1. Field of the Invention

The present invention relates to an optical detector for optically detecting abnormal portions in periodic patterns formed on industrial products. More specifically, the present invention relates to an optical detector for detecting, for example, defects in, or foreign matter attached to circuit patterns formed on wafers or reticles during manufacture of semiconductors.

2. Description of the Related Art

According to an optical theory, when an object is irradiated with coherent light beam such as laser light, the light beam is diffracted and scattered on the object. When a lens receives the diffracted light beam and forms an image of the object on its image plane, a so-called Fourier transform image of the object is formed on a Fourier transform plane defined between the lens and the image plane. When the object is formed with a periodic pattern, the Fourier transform image of the object has a periodic image corresponding to the periodic pattern on the object. When the object has defects on the periodic pattern, the Fourier transform image of the object is formed from a combination of the periodic image corresponding to the periodic pattern on the object and a non-periodic random image corresponding to defects. Accordingly, locating, on the Fourier transform plane, a spatial filter for blocking the periodic image (i.e., the Fourier transform image of the periodic pattern) can separate an image of the defects from the image of the position for picking up a Fourier transformed image of the object reflected from the half mirror 104. A central processing unit (CPU) 109 is connected to the television camera 110, the pattern generator 108 and the defect detecting portion 107.

In order to detect defects on a desired wafer, a sample wafer having the same periodic circuit pattern with the desired wafer is first located on the table 101. The television camera 110 picks up the Fourier transformed image of the circuit pattern, and transfers information on this image to the CPU 109.

Then, the wafer desired to be detected is located on the table 101. The CPU 109 controls the pattern generator 108 to apply electric voltage of a pattern corresponding to the Fourier transformed image of the circuit pattern detected for the sample wafer. As a result, the liquid crystal shutter 105 operates as a spatial shutter for blocking the Fourier transformed image of the periodic circuit pattern formed on the wafer. When the laser source 102 is driven to irradiate the wafer with laser light, only the portion of the Fourier transformed image of the wafer corresponding to the defects formed thereon passes through the liquid crystal shutter 105 to reach the CCD sensor 106. As a result, the CCD image sensor 106 picks up the image of the defects formed on the wafer, which is then processed by the defect detecting portion 107.

However, because this conventional optical detector has a television camera 110, the entire structure of the optical detector becomes large. In addition, it is necessary periodic pattern and form the defect image on the image plane.

FIG. 1 shows a conventional optical detector proposed by Japanese Patent Laid-Open Publication No. 5-45862 and employed with the above-described optical theory with the use of a liquid crystal shutter as the spatial filter.

The conventional optical detector has a laser source 102 for irradiating an object mounted on a table 101, such as a wafer formed with a periodic circuit pattern, with laser beam by a small incident angle θ. A condenser lens 103 is provided for forming an image of the object onto its image plane, on which a charge-coupled device (CCD) sensor 106 is located for picking up the formed image and for generating an image signal. A defect detecting portion 107 receives the image signal to thereby detect defects formed on the circuit pattern on the object. A twisted nematic (TN) liquid crystal shutter 105 is located on a Fourier transform plane defined between the lens 103 and the CCD sensor 106. The TN liquid crystal shutter 105 includes a twisted nematic liquid crystal layer 105c sandwiched between a pair of electrode layers 105b and 105d, which are sandwiched between a pair of polarizers 105a and 105e. A pattern generator 108 is provided to apply electric voltages of desired patterns between the electrode layers 105b and 105d to thereby control the liquid crystal shutter 105 as a desired spatial filter. A half mirror 104 is located between the liquid crystal shutter 105 and the lens 103 for guiding a half of the light from the lens 103 to each of the liquid crystal shutter 105 and a television camera 110. The television camera 110 is located at a to previously pick up the Fourier transformed image of the sample wafer, and therefore the processing is complicated.

FIG. 2 shows another conventional method for optically detecting defects in periodic patterns proposed by Y. Mitsuhashi, et al. in "Optical Inspection of Industrial Pattern Defect Using New Spatial Filter" (Journal of the Electrotechnical Research, 43—7,8) published on 1979.

In this conventional method, an object 201 having periodic patterns formed with defects is located on a front focal plane of a Fourier transform lens 202. Laser beam radiated on the object 201 passes through the object and is Fourier transformed by the Fourier transform lens 202 to form a Fourier Transformed image of the object on a back focal plane of the Fourier transform lens 202. A spatial filter 203 made from a photographic film is located on the back focal plane of the Fourier transform lens 202 so as to block only a spectral component of the periodic patterns formed on the object. Accordingly, only the spectral component of the defects passes through the spatial filter 203. The spatial filter 203 is positioned on a front focal plane of an inverse Fourier transform lens 204 which is the same as the Fourier transform lens 202. The inverse Fourier transform lens 204 receives light having passed through the spatial filter 203 and subjects the light to inverse Fourier transformation. As a result, a real image of the defects formed on the object 201 is formed on a back focal plane 205 of the inverse Fourier transform lens 204. Picking up the real image of the defects can detect the defects formed on the object 201.

Also in this conventional method, however, it is necessary to previously prepare the spatial filter 203 based on a sample object formed with the periodic pattern with no defects. Accordingly, this method is also complicated.

SUMMARY OF THE INVENTION

The present inventors have motivated to utilize an optically-addressed spatial light modulator (SLM) as the spatial filter so as to provide an improved optical detector which does not need preparing a spatial filter in advance and therefore which is easy in operation.

The basic structure of the inventors' motivated optical detector is the same as that of the conventional structure shown in FIG. 2 except that the spatial filter 203 is replaced with an optically-addressed SLM. The basic structure will be explained while referring to FIGS. 3 and 4. FIG. 3 is of a first type of optical detector utilizing a reflection type optically-addressed SLM, and FIG. 4 is of a second type of optical detector utilizing a transmission type optically-addressed SLM.

The optical detector shown in FIG. 3 includes a reflection type optically-addressed spacial light modulator (SLM) A, a half mirror B, and an analyzer C which are entirely located between a Fourier transform lens FT and an Inverse Fourier transform lens IFT. Similarly to the optical system of FIG. 2, the lenses FT and IFT are located, with the back focal plane of the lens FT being on the same plane with the front focal plane of the lens IFT (which will be referred to as "Fourier transformed plane," hereinafter). The SLM A is located on the Fourier transform plane FP.

The reflection type optically-addressed SLM A includes a transparent electrode film 4, a light modulation layer 1, a reflection layer 3, a photoconductive layer 2, and a transparent electrode film 5 stacked in the order listed. The light modulation layer 1 servers as a light modulating part, and is made from a light modulating material such as twisted nematic (TN) liquid crystal. The photoconductive layer 2 servers as an optically-addressing part, and is made from, for example, an amorphous silicon (α- Si). The transparent electrode film 4 is formed to the light modulation layer 1 and the transparent electrode film 5 is formed to the photoconductive layer 2. A voltage source VS is provided with one terminal connected to the transparent electrode film 4 and the other terminal connected to the transparent electrode film 5 so that an AC bias voltage of a predetermined voltage (amplitude) develops between the transparent electrode films 4 and 5.

The half mirror B is positioned in front of the light modulation layer 1. The analyzer C is positioned so as to be in the path of light reflected off the half mirror B.

During measurement, the surface of an object O, such as a semiconductor wafer with a periodic circuit pattern formed thereto, is first irradiated with a laser beam from a write light source WS at a small angle θ of incidence. A light image obtained through diffraction and scattering of the light on the object is optically Fourier transformed by the Fourier transform lens FT. The Fourier transformed image becomes incident on the photoconductive layer 2 as a write light image. The write light image causes regional changes in electric resistance of the photoconductive layer 2 in amounts proportional to the intensity of light incident on that region of the photoconductive layer 2. For example, electrical resistance greatly drops at regions of the photoconductive layer 2 that are irradiated with greatly intense light. The AC bias voltage between the transparent electrode films 4 and 5 is applied to regions of the light modulation layer 1 at amounts proportional to the resistance of corresponding regions of the photoconductive layer 2. Accordingly, birefringence change induced in a region of the light modulation layer 1 is proportional to the intensity of the write light image at that region.

When the object formed with the periodic circuit pattern is irradiated with laser light by the small incident angle θ, the periodic circuit patterns (mainly, edges thereof) diffract and scatter the laser light in a periodical manner while the defects of random pattern diffract and scatter the laser light randomly or uniformly. Accordingly, the Fourier transformed image, obtained at the Fourier transform plane FP and recorded in the SLM A as the write light image, has two spectral components: a first spectral component representing the periodic circuit patterns and having a high intensity; and a second spectral component representing a random pattern of the defects and having an intensity much less than the first spectral component. Therefore, refractive index changes in the light modulation layer 1 to the great extent at regions irradiated by the high intensity spectral component, which corresponds to the periodic circuit pattern, to thereby induce birefringence of large degree. On the other hand, refractive index changes to a small extent at regions of the light modulation layer 1 irradiated by the low intensity spectral component, which corresponds to the defects, to thereby induce birefringence of small degree. Thus, information represented by the spectral intensity of the write light is recorded in the light modulation layer 1 by the electrooptic effect as the change in birefringence degree distribution in the light modulation layer 1.

Then, a linearly-polarized parallel light beam having a uniform intensity distribution (referred to as read light hereinafter) from a read light source RS is passed through the half mirror B to fall incident on the light modulation layer 1. The read light passes through the light modulation layer 1 and is reflected off the reflection layer 3 and passes back through the light modulation layer 1. The linearly-polarized read light is modulated in the light modulation layer 1, in accordance with the degree of birefringence induced in the light modulating layer 1. As a result, the linearly-polarized read light is changed into an ellipsoidally-polarized light with its polarization state corresponding to the degree of birefringence. In other words, the read light outputted from the SLM A has a polarization state spatially distributed in correspondence with the spatial distribution of the high and low intense spectral components in the write image. The read light then reflects off the half mirror B so as to fall incident on the analyzer C. In this way, the spatial distribution of polarization state in the light image incident on the analyzer C corresponds to the spatial distribution of the write light image. The analyzer C is for blocking transmission of light of a predetermined polarization state corresponding to that of the light which has been modulated in the light modulating layer 1 by the large degree of birefringence. Accordingly, the analyzer C blocks the transmission of the light component that corresponds to the periodic circuit pattern. Therefore, the image (reflection image, hereinafter) transmitted through the analyzer C contains only the spectral component corresponding to the defects. By inverse Fourier transforming the reflection image through the inverse Fourier transform lens IFT, an real image relating to only defects can be reproduced.

The other type of optical detector shown in FIG. 4 includes a transmission type optically-addressed SLM D, a half mirror E, and an analyzer F which are entirely located between a Fourier transform lens FT and an inverse Fourier transform lens IFT. Similarly to the optical detector of FIG. 3, the SLM D is located on a Fourier transform plane FP on which the back focal plane of the Fourier transform lens FT and the front focal plane of the inverse Fourier transform lens IFT are positioned.

The reflection type spatial light modulator D includes a transparent electrode film 10, a photoconductive layer (optically-addressing part) 8, a light modulation layer (light modulating part) 7, and another transparent electrode film 9 stacked in the order listed. The structure of the transmission type SLM D is the same as that of the reflection type SLM A except that the reflection layer is omitted from the transmission type SLM D. The transparent electrode film 9 is formed to the light modulation layer 7, and the transparent electrode film 10 is formed to the photoconductive layer 8.

A voltage source VS is provided with one terminal connected to the transparent electrode film 9 and the other terminal connected to the transparent electrode film 10 so that an AC bias voltage of a predetermined voltage (amplitude) develops between the transparent electrode films 9 and 10. The half mirror E is disposed in front of the transparent electrode film 10. The analyzer F is disposed in confrontation with the electrode film 9.

During measurements, the surface of the objective O to be measured, such as a semiconductor wafer with a circuit pattern formed therein, is first irradiated with a laser beam (write light) from a write light source WS, at a small angle θ of incidence. The write light diffracted and scattered from the semiconductor surface is transmitted through the Fourier transform lens FT where the image in the write light is optically Fourier transformed. The write light is then transmitted through the half mirror E so as to fall incident on the electrode layer 10. The write light passes through both the photoconductive layer 8 and the light modulating layer 7 to output from the electrode layer 9. It is noted that the wavelength of the write light is selected to within photosensitivity range of the photoconductive layer 8. Accordingly, when passing through the photoconductive layer 8, the write light causes regional changes in electric resistance of the photoconductive layer 8 in amounts proportional to the intensity of light incident on that region of the photoconductive layer 8. The AC bias voltage between the transparent electrode films 10 and 9 is applied to regions of the light modulation layer 7 at amounts proportional to the resistance of corresponding regions of the photoconductive layer 8. As a result, birefringence is induced in regions of the light modulation layer 7 by amounts proportional to intensity at corresponding regions of the write light.

Also in this case, the spectral distribution of the write image has the two spectral components: the first spectral component representing the periodic circuit pattern and having a high intensity; and the second spectral component representing a random defect pattern and having an intensity much less than that of the first spectral component. Thus, information on the spectral intensity of the write light image is recorded in the light modulation layer 7 as changes in alignment of the liquid crystal.

After this writing processes are completed, a linearly-polarized parallel light beam (read light) having a uniform intensity distribution from a read light source RS is irradiated on the half mirror E so as to be reflected to fall incident on the light electrode layer 10. The read light passes through both the photoconductive layer 8 and the light modulating layer 7 to output from the electrode layer 9. It is noted that the wavelength of the read light is selected to be out of the photosensitivity of the photoconductive layer 8. Birefringence induced in the light modulation layer 7 modulates the read light into an ellipsoidally-polarized light with its polarization state corresponding to the birefringence degree induced in the light modulating layer 7. In other words, the read light outputted from the SLM D has a polarization state spatially distributed in correspondence with the spatial distribution of the high and low intense spectral components in the write image. The read light is then irradiated incident to the analyzer F. The analyzer F is for blocking passage of a predetermined polarization component of the light that has been modulated in the modulating layer 7 with the birefringence of the large degree. Accordingly, the analyzer F blocks transmission of the light component that corresponds to the periodic circuit pattern. Therefore, the analyzer F outputs only the light component relating to the defects. The outputted light is then transmitted through the inverse Fourier transform lens IFT. By subjecting the outputted light to the inverse Fourier transformation, a real image relating to the defects on the surface of the semiconductor is reproduced.

As described above, the proposed optical detectors shown in FIGS. 3 and 4 extract information on abnormal portions of an objective, and reproduce a real image thereof for easy visual confirmation.

However, the optical detectors require two independent light sources (such as a laser sources): the write light source WS for forming the write light; and the read light source RS for forming the read light. This creates another problem in that the proposed optical detectors are still somewhat large.

Especially in the transmission type SLM shown in FIG. 4, the write light laser source WS must generate laser light with a wavelength in the photosensitivity range of the photoconductive layer. In contrast, the wavelength of laser light generated by the read light laser source RS must be outside the photosensitivity range of the photoconductive layer.

It is therefore, an object of the present invention to overcome the above-described drawbacks, and to provide an optical detector with only one irradiation source and capable of producing a clear reproduced image with little noise.

In order to attain the above object and other object, the present invention provides an optical detector for detecting an abnormal portion in a periodic pattern in an objective, the optical detector comprising: a light source for irradiating coherent light onto an objective; a Fourier transform lens for receiving light diffracted and scattered at the objective and for Fourier transforming the light to generate a Fourier image, the Fourier image having a high intensity spectral component corresponding to the periodic pattern on the objective and a low intensity spectral component corresponding to the abnormal portion; a polarizer for transmitting a predetermined polarization component of the Fourier image; an optically-addressed spatial light modulator having an optically-addressing part and a light modulating part, the optically-addressing part and the light modulating part respectively receiving a write part and a read part of the predetermined polarization component of the Fourier image transmitted through the polarizer, at corresponding portions thereof; threshold driving control means for controlling the spatial light modulator in its threshold operation so as to induce birefringence in the light modulating part at a region corresponding to an area in the optically-addressing part where the high intensity spectral component of the write part is incident while preventing birefringence from being induced in the light modulating part at a region corresponding to an area in the optically-addressing part where the low intensity spectral component of the write part is incident, the induced birefringence rotating the polarization plane of the high intensity spectral component of the read part incident in the light modulating part; a detector for receiving the read part of the Fourier image outputted from the light modulating part of the optically-addressed type spatial light modulator and for blocking the high intensity spectral component thereof with its polarization plane having been rotated; and another Fourier transform lens for inverse Fourier transforming the low intensity spectral component into an real spatial image of the abnormal portion on the objective.

The spatial light modulator may further include a pair of electrodes for applying electric voltage through the optically-addressing part and the light modulating part, and wherein the threshold driving control means includes a voltage controlling means for controlling the electric voltage applied between the pair of electrodes to a value that induces birefringence in the light modulating part at a region corresponding to an area in the optically-addressing part where the high intensity spectral component is incident while preventing birefringence from being induced in the light modulating part at a region corresponding to an area in the optically-addressing part where the low intensity spectral component is incident.

The spatial light modulator may further include a reflective layer located between the optically-addressing part and the light modulating part for reflecting off the read part of the Fourier image travelled through the light modulating part. In this case, the optical detector may further comprise optical guiding means for guiding the write part of the Fourier image to the optically-addressing part and for guiding the read part of the Fourier image to the light modulating part in such a manner that the write part of the Fourier image and the read part of the Fourier image are received in the optically-addressing part and the light modulating part, respectively, substantially in symmetry with respect to the reflective layer. The optical detector may further comprise a filter for controlling intensity of the write part of the Fourier image guided by the optical guiding means to the optically-addressing part.

The spatial light modulator may include the light modulating part and the optically-addressing part contacted with each other by an interface defined therebetween, the light modulating part and the optically-addressing part having refractive indices different from each other, the spatial light modulator receiving the Fourier image transmitted through the polarizer to be incident on the light modulating part, the write part of the Fourier image passing through the interface to enter the optically-addressing part and the remaining read part of the Fourier image being reflected at the interface due to the difference in the refractive indices of the optically-addressing part and the light modulating part.

According to another aspect, the present invention provides an optical detector for detecting an abnormal portion in a periodic pattern in an objective, the optical detector comprising: a light source for irradiating coherent light onto an objective; a Fourier transform lens for receiving light diffracted and scattered at the objective and for Fourier transforming the light to generate a Fourier image, the Fourier image having a high intensity spectral component corresponding to the periodic pattern on the objective and a low intensity spectral component corresponding to the abnormal portion; an optically-addressed spatial light modulator having a optically-addressing part and a light modulating part, each of the optically-addressing part and the light modulating part receiving the Fourier image at the corresponding portions; threshold driving control means for controlling the spatial light modulator in its threshold operation so as to change a state in the light modulating part at a region corresponding to an area in the optically-addressing part where the high intensity spectral component of the Fourier image is incident while preventing the state from being changed in the light modulating part at a region corresponding to an area in the optically-addressing part where the low intensity spectral component of the Fourier image is incident, the changed state in the light modulating part modulating the high intensity spectral component of the Fourier image incident in the light modulating part; separating means for receiving the Fourier image outputted from the light modulating part of the optically-addressed type spatial light modulator and for separating the modulated high intensity spectral component from the unmodulated low intensity spectral component; and another Fourier transform lens for inverse Fourier transforming the low intensity spectral component into a real spatial image of the abnormal portion on the objective.

BRIEF DESCRIPTION OF THE DRAWINGS

The above and other objects, features and advantages of the invention will become more apparent from reading the following description of the preferred embodiment taken in connection with the accompanying drawings in which:

FIG. 11 (b) shows the manner how the FLC-SLM presenting the transfer characteristic of FIG. 11 (a) is driven with the bias electric voltage and is irradiated with write light and read light.

DETAILED DESCRIPTION OF THE PREFERRED EMBODIMENTS

Figure 1:
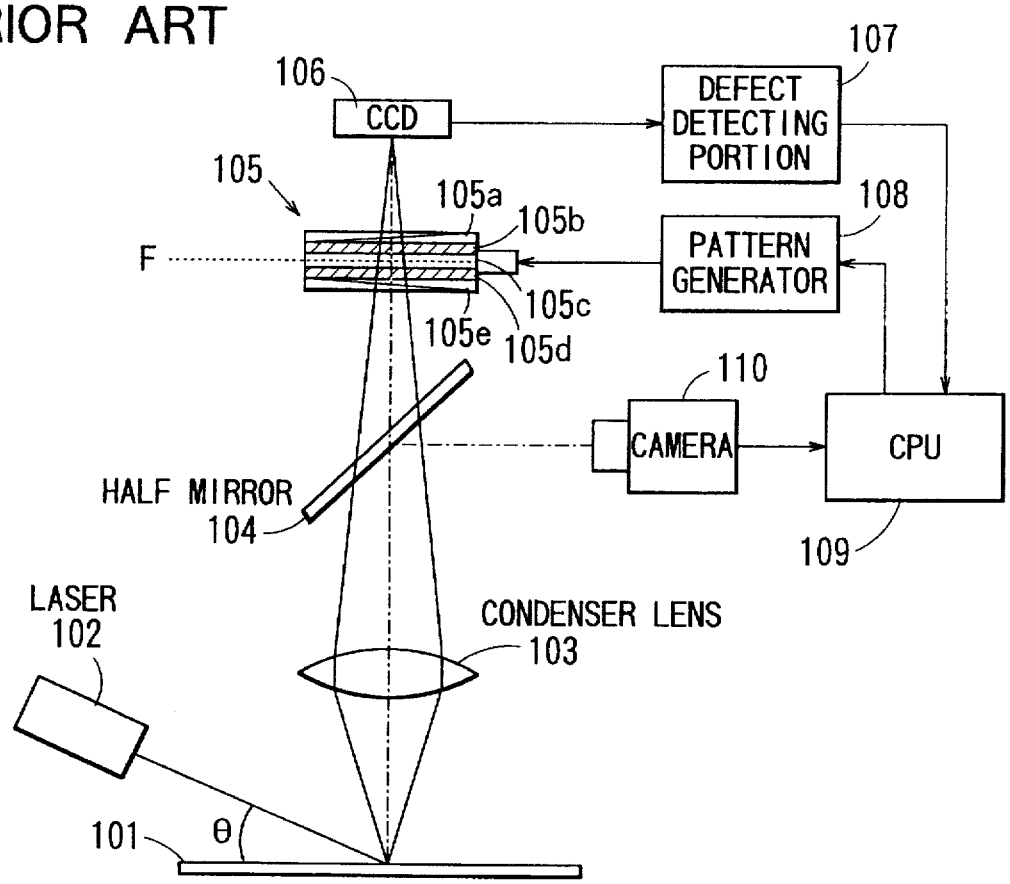
FIG. 1 illustrates a structure of a conventional optical detector.
Figure 2:
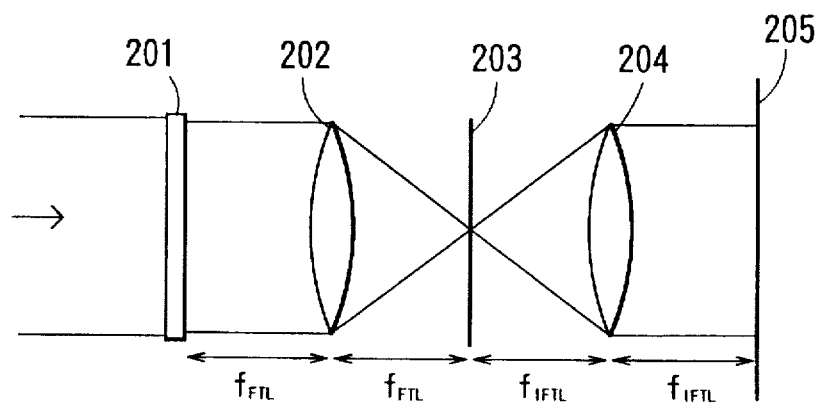
FIG. 2 illustrates an optical system of a conventional optical detector of another type.
Figure 3:
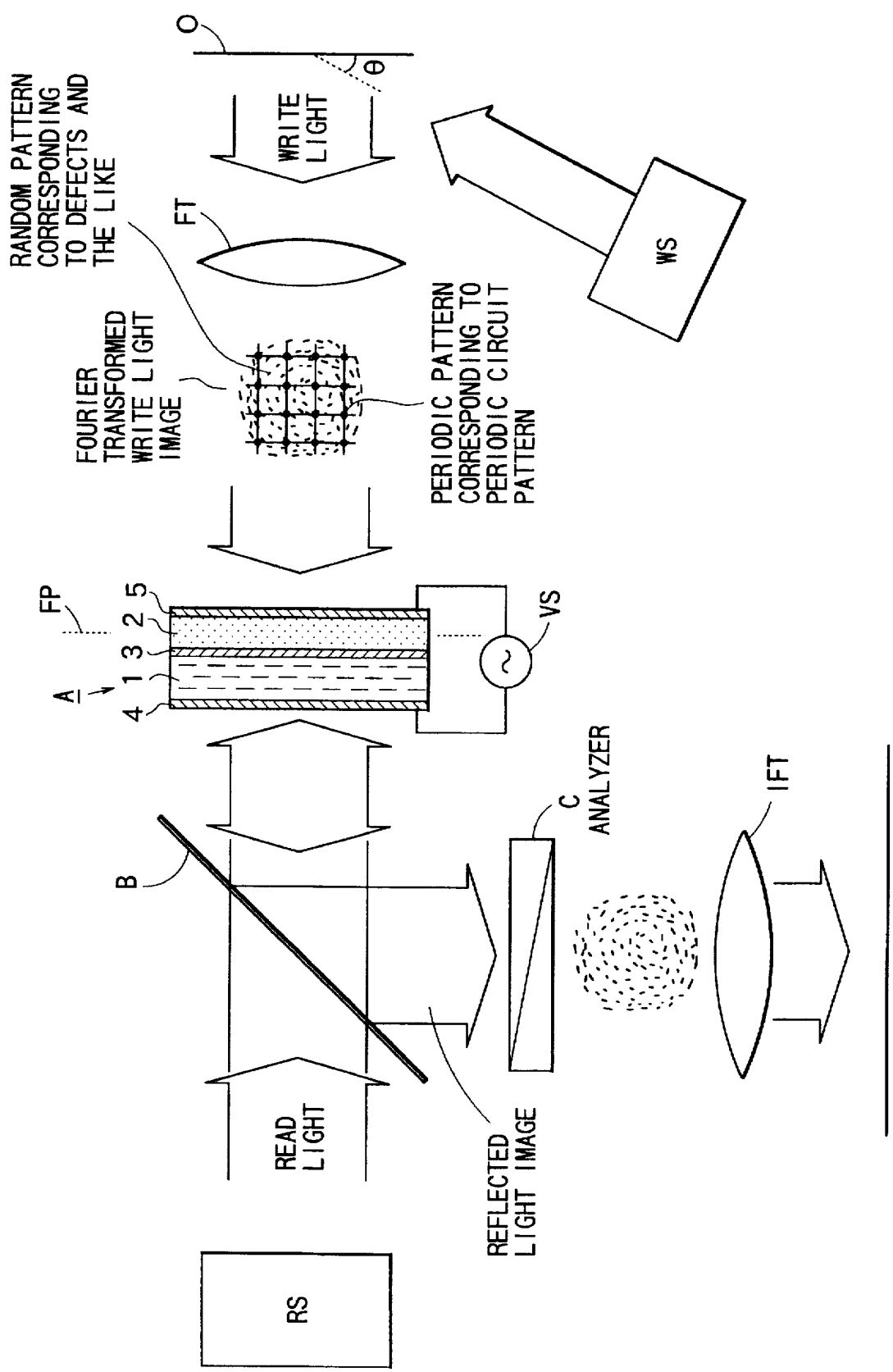
FIG. 3 illustrates an optical system of the present inventors' motivated optical detector of a first type employing an reflection type optically-addressed type SLM.
Figure 4:
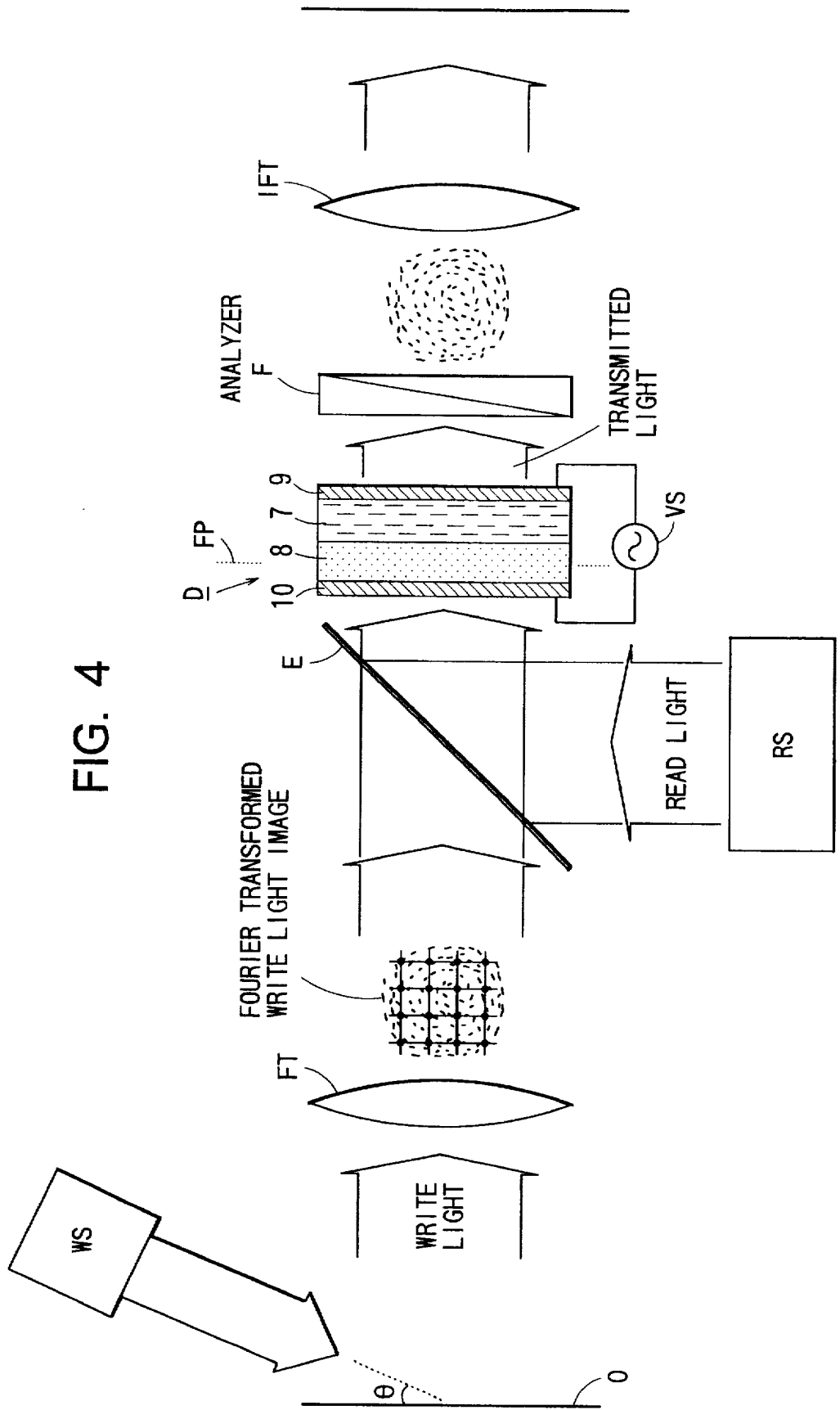
FIG. 4 illustrates an optical system of the present inventors' motivated optical detector of a second type employing an transmission type optically-addressed type SLM.

According to the present invention, in order to provide the optical detector with a single light source, the Fourier transformed image of the object having the high intense spectral component for the periodic pattern and the low intense spectral component for the abnormal pattern is divided into two identical Fourier transformed images, which are then incident on the optically-addressing part and the light modulating part of the optically-addressed type SLM, at corresponding positions. The SLM is operated in its threshold mode operation so that birefringence may be induced in the light modulating part at regions corresponding to the areas where the high intense spectral component is incident on the optically-addressing part, but birefringence may not be induced in the light modulating part at regions corresponding to the areas where the low intense spectral component is incident on the optically-addressing part. Accordingly, the SLM can modulate the polarization state of only the high intense spectral component incident on the light modulating part, to thereby separate the high intense spectral component from the low spectral component.

Generally, SLMs can be operated in a threshold operation. This threshold operation is owing to non-linear transfer characteristics of the SLMs.

This non-linear transfer characteristic is obtained in the light modulating part, when the SLM is of a type in which the light modulating part is made from liquid crystal. For example, when the light modulating part is made from twisted nematic liquid crystal, in order to induce birefringence in the light modulating part, electric field energy higher than a predetermined value of initial energy (threshold energy) should be developed through the light modulating part. The value of the initial energy (threshold energy) is determined as an amount of energy required to actuate the twisted nematic liquid crystal molecules to move. The initial energy includes: anchoring energy for rising up liquid crystal molecules from the interface of the light modulating layer with respect to the alignment layer; and a breaking energy for breaking the twisted structure. Accordingly, when an electric field energy lower than the initial energy is developed through the liquid crystal layer, the liquid crystal molecules do not move, so as not to induce the birefringence in the liquid crystal layer. When an electric field energy higher than the initial energy is developed through the liquid crystal layer, the liquid crystal molecules move, so as to induce the birefringence in the liquid crystal layer.

When the light modulating part is made from the surface-stabilized ferroelectric liquid crystal, if an electric field energy lower than a predetermined value of initial energy, required to move the liquid crystal molecules in this type of layer, is developed through the liquid crystal layer, the liquid crystal molecules do not move, so as not to induce the birefringence in the liquid crystal layer. Accordingly, it is necessary to develop, through the light modulating part, an electric field energy higher than the predetermined value of the initial energy. Especially in this type of light modulating layer, in order to cause the light modulating part to attain its memory effect, electric field energy higher than another type of predetermined energy (threshold energy) should be developed through the light modulating layer. This type of predetermined energy (threshold energy) includes: the anchoring energy the same as that for the twisted nematic liquid crystal; and a reversing energy for turning or reversing spontaneous polarization of the liquid crystal molecules. When an electric field energy lower than this type of predetermined energy is applied through the liquid crystal layer, the liquid crystal layer does not attain a memory effect. Accordingly, when the application of the electric field stops, the liquid crystal molecules returns to their initial state, so as not to maintain the birefringence.

It is noted that when the light modulating part is thus made from liquid crystal, the threshold operating characteristics can be attained also due to its interface energy.

When the SLM is an MSLM with its light modulating layer being made from an electrooptic crystal, for example, the threshold operating characteristic is attained by an electric voltage applied at a crystal back electrode or a mesh electrode thereof.

In the optically-addressed type SLMs, the electric field energy applied through the light modulating part is determined dependently on the intensity of write light incident on the optically-addressing part (photoconductive layer), the bias electric field applied through the optically-addressing part and the light modulating part, and the photosensing characteristics (i.e., electrical resistance changing characteristics) of the optically-addressing part (photoconductive layer).

Accordingly, in the present invention, the bias electric voltage applied to the SLM is controlled, dependently on the intensities of the high intensity spectral component for the periodic pattern and of the low intensity spectral component for the abnormal pattern which are incident on the optically-addressing part, so that an electric field energy higher than the predetermined threshold energy may be developed through the light modulating part at regions corresponding to the areas where the high intense spectral component is incident on the optically-addressing part and an electric field energy lower than the predetermined threshold energy may be developed through the light modulating part at regions corresponding to the areas where the low intense spectral component is incident on the optically-addressing part. Accordingly, birefringence may be induced in the light modulating part at regions corresponding to the areas where the high intense spectral component is incident on the optically-addressing part, but birefringence may not be induced in the light modulating part at regions corresponding to the areas where the low intense spectral component is incident on the optically-addressing part.

Or otherwise, according to the present invention, the intensities of the high intensity spectral component for the periodic pattern and of the low intensity spectral component for the abnormal pattern which are incident on the optically-addressing part may be controlled, dependently on the bias electric voltage applied to the SLM, so that an electric field energy higher than the predetermined threshold energy may be developed through the light modulating part at regions corresponding to the areas where the high intense spectral component is incident on the optically-addressing part and an electric field energy lower than the predetermined threshold energy may be developed through the light modulating part at regions corresponding to the areas where the low intense spectral component is incident on the optically-addressing part. Accordingly, birefringence may be induced in the light modulating part at regions corresponding to the areas where the high intense spectral component is incident on the optically-addressing part, but birefringence may not be induced in the light modulating part at regions corresponding to the areas where the low intense spectral component is incident on the optically-addressing part.

Of course, both the bias electric voltage and the intensities of the high intensity spectral component and of the low intensity spectral component incident on the optically-addressing part may be controlled so that an electric field energy higher than the predetermined threshold energy may be developed through the light modulating part at regions corresponding to the areas where the high intense spectral component is incident on the optically-addressing part and an electric field energy lower than the predetermined threshold energy may be developed through the light modulating part at regions corresponding to the areas where the low intense spectral component is incident on the optically-addressing part.

Figure 11:
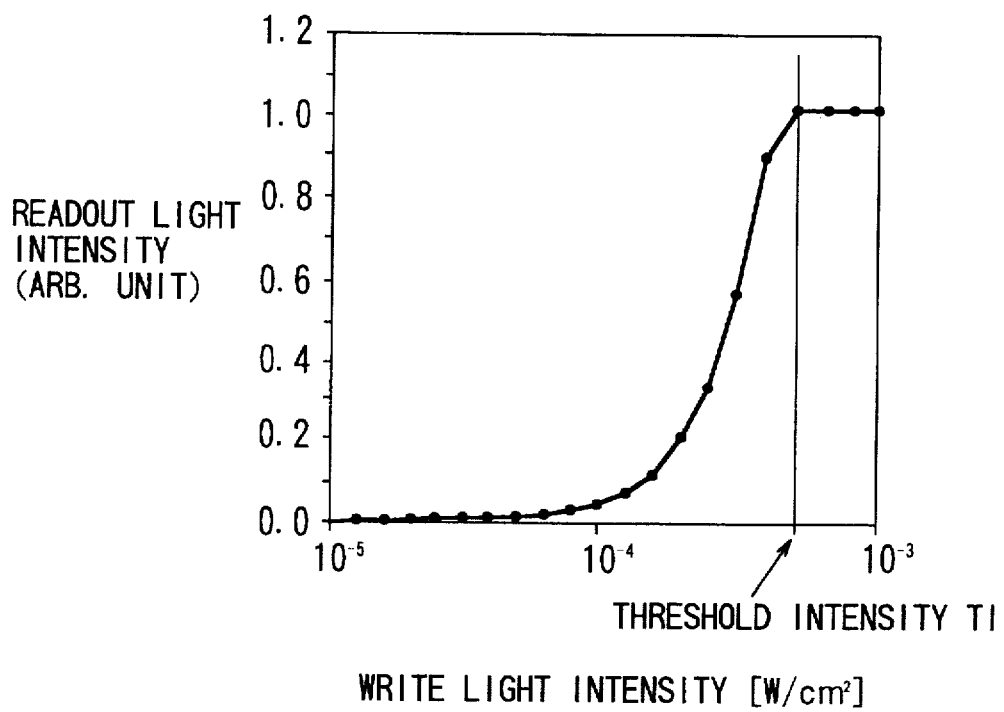
FIG. 11 (a) is a graph showing transfer characteristics of a concrete example of a reflection-type ferroelectric liquid crystal spatial light modulator (FLC-SLM) produced by HAMAMATSU PHOTONICS K. K. (trade name "FLC-SLM X4601")
Figure 11:
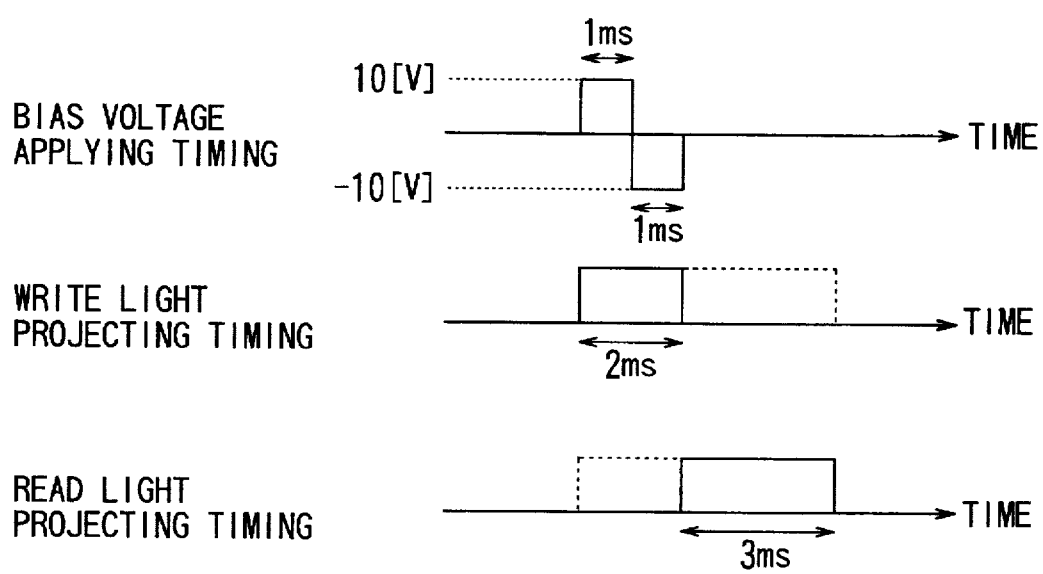

FIG. 11 (a) shows the transfer characteristics of a concrete example of a reflection type ferroelectric liquid crystal spatial light modulator (FLC-SLM) produced by HAMAMATSU PHOTONICS K. K. (trade name "FLC-SLM X4601") when applied with the bias electric voltage of 10 [volts] at timings shown in FIG. 11 (b). In this driving operation, while the bias electric voltage of 10 [volts] is applied to the FLC-SLM, with its polarity being switched once, write light is projected on the optically-addressing part. Then, read light is projected on the light modulating part. (It is noted that the read light and the write light may be projected simultaneously as indicated by dotted line in FIG. 11 (b).) It is apparent that according to this driving condition, after completion of the application of the bias voltage, memory effect is obtained in the light modulating part, in the case where write light with its intensity higher than a predetermined threshold intensity TI is incident on the optically-addressing part. Memory effect is not obtained, in the case where write light with its intensity lower than the predetermined threshold intensity TI is incident on the optically-addressing part. Accordingly, in the present invention, controlling the bias electric voltage to a value of 10 [volts] and adjusting the intensities of the high intensity spectral component and of the low intensity spectral component to be higher and lower than the predetermined threshold intensity Tl, respectively, can control the FLC-SLM to operate in its threshold mode operation.

An optical detector according to preferred embodiments of the present invention will now be described below while referring to accompanied drawings.

An optical detector according to a first preferred embodiment of the present invention will be described below while referring to FIGS. 5 through 7. The first embodiment employs a reflection type optically-addressed SLM.

Figure 5:
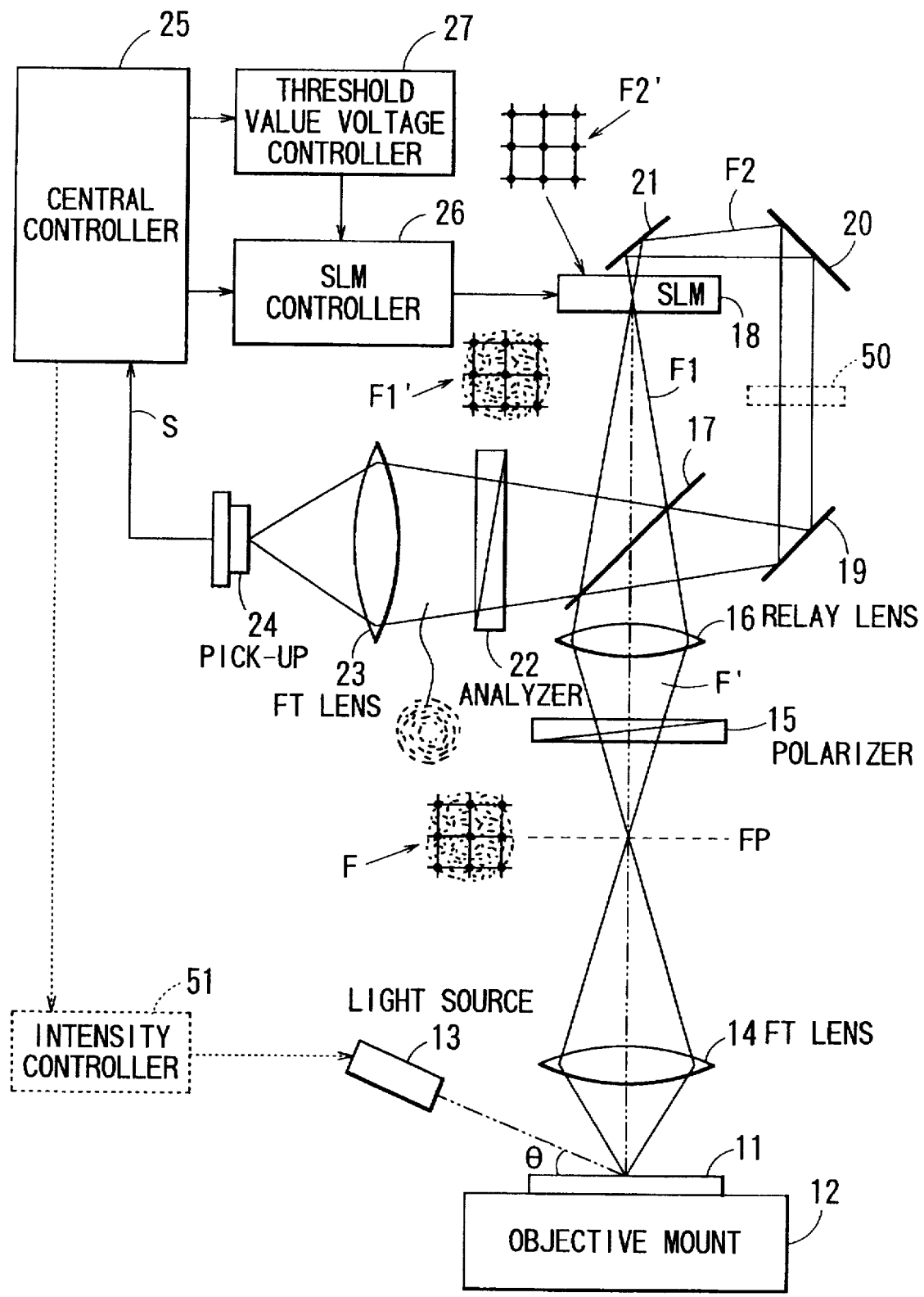
FIG. 5 illustrates an overall structure of an optical detector of a first preferred embodiment of the present invention.

First, a description of the overall structure of the optical detector will be provided while referring to FIG. 5. The optical detector includes: an objective mount 12; a laser light source 13; a Fourier transform lens 14; a polarizer 15; a relay lens 16; a half mirror 17; a series of fully reflective mirrors 19, 20 and 21; a reflection type optically-addressed SLM 18; an analyzer 22; the other Fourier transform lens 23 (i.e., an inverse Fourier transform lens); a solid state image pick up device 24; a central controller 25; an SLM controller 26; and a threshold value voltage controller 27.

The objective mount 12 is for supporting an objective 11 to be measured, for example, a semiconductor wafer, and is capable of freely moving to and stopping at positions with coordinates in three dimensions (that is, coordinates along X, Y, and Z axes). The laser light source 13 is for irradiating the surface of the objective 11 with a laser beam at a small angle of incidence θ. It is noted that the wavelength of the laser light from the light source 13 is selected to within photosensitivity range of the optically-addressing part (photoconductive layer 35, shown in FIG. 6, for example of the SLM 18.

The Fourier transform lens 14 is positioned in confrontation with the objective mount 12 so that the objective 11 mounted on the objective mount 12 is positioned on a front focal plane of the Fourier transform lens 14. The Fourier transform lens 14 is for Fourier transforming the light pattern generated by diffraction and scattering of the laser beam at the surface of the objective 11. The Fourier transform lens 14 defines a Fourier plane FP at its back focal plane. A Fourier image (spatial spectral image) F of the light pattern, including information on the surface shape of the objective 11 formed with periodic circuit patterns and foreign matter and defects, is generated at the Fourier plane FP. The Fourier image F includes a high intensity spectral component and a low intensity spectral component. The high intensity spectral component represents the periodic pattern of the circuit pattern formed on the semiconductor wafer in a set periodic pattern and the low intensity spectral component has a random pattern corresponding to defects in and foreign matter on the semiconductor wafer.

The polarizer 15, the relay lens 16, the half mirror 17, and the reflection type SLM 18 are aligned to one side of the Fourier plane FP of the Fourier lens 14 along the axis of Fourier transform lens 14.

The polarizer 15 is for selectively transmitting a desired polarized light component of the Fourier transformed light image F so as to generate a Fourier transformed light image F'. For example, when the SLM 18 is a reflective type twisted nematic (TN) liquid crystal SLM, the polarizer 15 can be designed to transmit linearly-polarized light with its polarization plane being in parallel with alignment of liquid crystal on the output side of a light modulating part in the SLM 18. It is noted that the Fourier transformed image F' also has the high spectral component corresponding to the periodic circuit patterns and the low spectral component corresponding to the defects and foreign matters.

The half mirror 17 is for transmitting a half part of the Fourier transformed light image F' to front side (light modulating part) of the SLM 18 and for reflecting the remaining part of the Fourier transformed light image F' toward a fully reflective mirror 19. For convenience sake, the Fourier transformed light image F' that is transmitted through the half mirror 17 will be referred to as a "read light image F1," hereinafter. The other Fourier transform light image F' that is reflected off the half mirror 17 will be referred to as a "write light image F2," hereinafter. The read light image F1 and the write light image F2 therefore have completely identical patterns which have the high spectral component corresponding to the periodic circuit patterns and the low spectral component corresponding to the defects and foreign matters.

The fully reflective mirror 19 and two additional fully reflective mirrors 20 and 21 are disposed so as to reflect the write light image F2 toward the rear side (optically-addressing part) of the SLM 18. In this way, the identical spectral patterns of the read light image F1 and the write light image F2 are incident on the front and rear surfaces respectively of the SLM 18. It is noted that the half mirror 17 and the fully reflective mirrors 19, 20, and 21 are positioned and angled so that the identical spectral patterns of the write light image F2 and the read light image F1 are in complete spatial symmetry when irradiated on the rear and front surfaces respectively of the SLM 18.

As will be described later, the SLM 18 is controlled by a combination of the SLM controller 26 and the threshold voltage adjusting portion 27 to modulate only the high intensity spectral component of the read light image F1 by 90°, to produce a regionally modulated light image F1'. The modulated light image F1' is outputted from the SLM 18 and reflected off the half mirror 17 so as to fall incident on an analyzer 22. The analyzer 22 is for blocking the 90° modulated polarized portion of the light image F1'. Therefore, the unmodulated low intensity spectral component of the light image F1' is only transmitted through the analyzer 22 so as to fall incident on the Fourier transform lens 23. Because the SLM 18 is positioned on the front focal plane of the Fourier transform lens 23, the Fourier transform lens 23 subjects the light image to inverse Fourier transformation to reproduce a real spatial image on the back focal plane of the lens 23. The real spatial image is picked up by the solid-state image pick up device such as a charge coupled device (CCD) 24 disposed in the back focal plane of the lens 23. The CCD 24 generates an image signal S, representative of the picked up real spatial image, and transfers the image signal S to the central controller 25.

The central controller 25 is for determining the existence and position of defects and foreign matter on the objective 11 by performing predetermined imaging processes based on the image signal S. The central controller 25 is also for performing processes for generating a video signal for indicating the real spatial image on a monitor television (not shown). The central controller 25 is also for controlling the SLM controller 26 and the threshold value voltage controller 27. The SLM controller 26 is for generating an AC bias voltage for driving the SLM 18. The threshold value voltage controller 27 is for adjusting the voltage amplitude of the AC bias voltage to be generated by the SLM controller 26.

Figure 6:
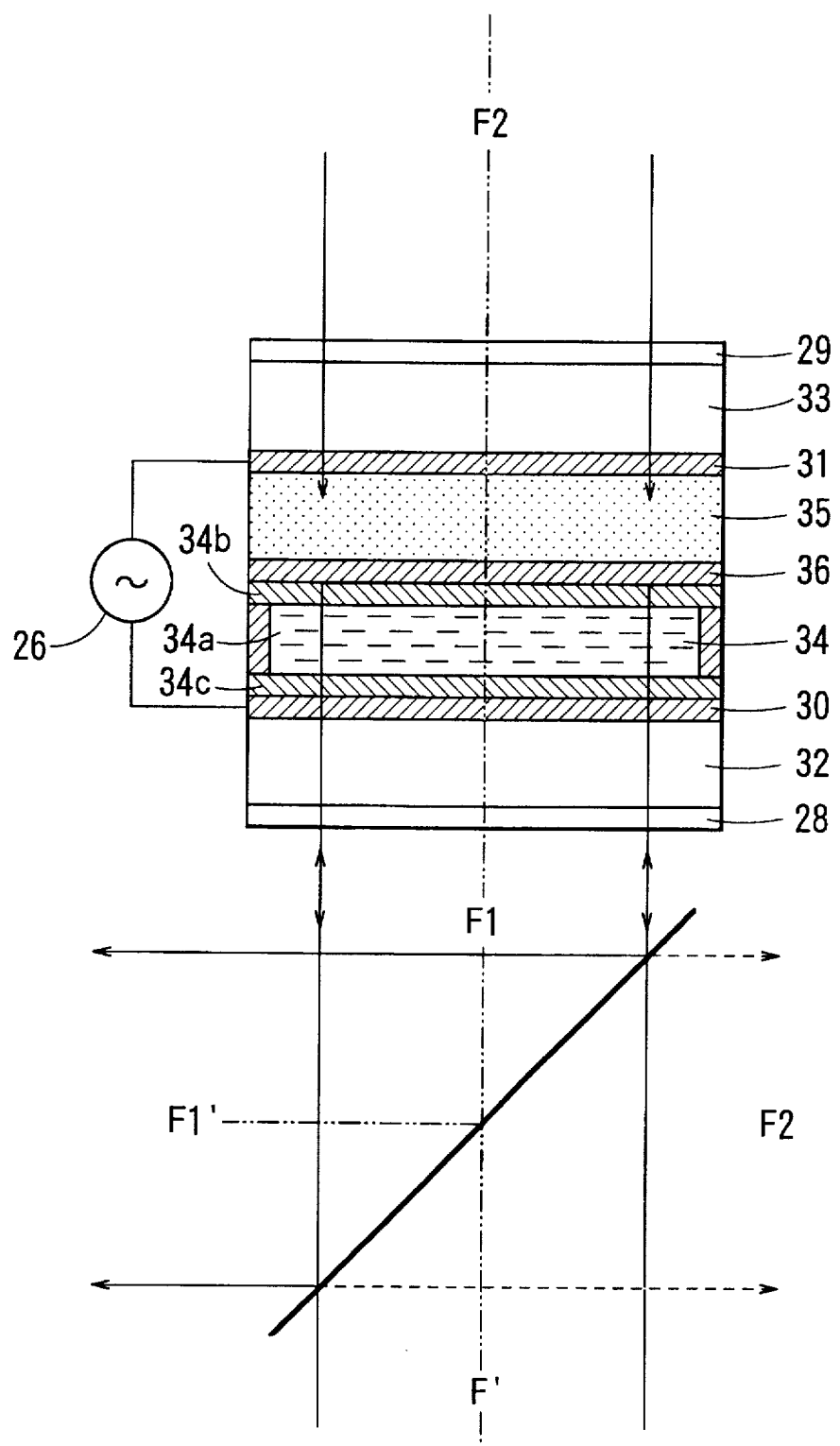
FIG. 6 illustrates a structure of a reflection type optically-addressed type SLM employed in the optical detector of FIG. 5.
Figure 7:
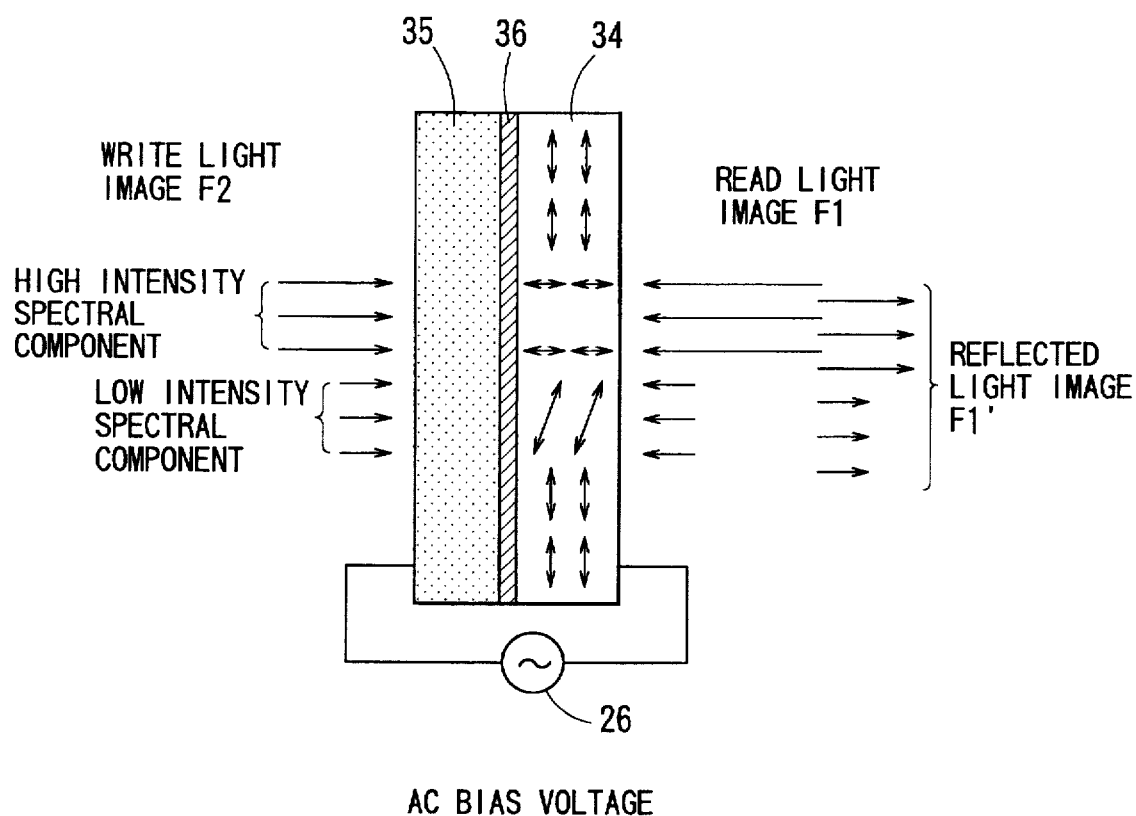
FIG. 7 illustrates an operation of the reflection type optically-addressed type SLM employed in the optical detector of FIG. 5.

Next, an explanation of the structure and function of the reflective type optically-addressed SLM 18 employed in the present embodiment will be provided while referring to FIGS. 6 and 7.

As shown in FIG. 6, the SLM 18 includes a photoconductive layer 35, a light reflecting layer 36, and a light modulation layer 34 stacked in the order listed. The light modulation layer 34 servers as a light modulating part, and is made from a light modulating material 34a, such as twisted nematic (TN) liquid crystal or ferroelectric liquid crystal, sandwiched between a pair of alignment layers 34b and 34c. The photoconductive layer 35 serves as an optically-addressing part, and is made from a photoconductive material such as amorphous silicon (α-Si). This stack of layers is sandwiched between a pair of confronting substrates 33 and 32. The confronting substrates 33 and 32 are made from transparent glass. The outward facing side of each confronting substrate 33 and 32 has coated thereon an AR coat layer 29 and 28 respectively. The inward facing side of each confronting substrate 33 and 32 has accumulated thereon a transparent electrode film 31 and 30 respectively. The SLM control portion 26 in the form of a power source is provided with one terminal connected to the transparent electrode film 31 and the other terminal connected to the transparent electrode 30. The SLM control portion 26 thereby applies an AC bias voltage between the pair of transparent electrode films 30 and 31.

The read light image F1 having passed through the half mirror 17 falls incident on the outward surface of the substrate 32. The write light image F2 reflected off the fully reflective mirror 21 (not shown in FIG. 6) falls incident on the outward surface of the substrate 33.

In the SLM 18 with the above-described structure, as shown in FIG. 7, the electrical resistance of the photoconductive layer 35 changes in proportion to the intensity of each spectral portion of the write light image F2 incident on the back surface. The effective voltage of the AC bias voltage applied to regions of the light modulation layer 34 therefore corresponds to the resistance value at corresponding regions of the photoconductive layer 35.

It is noted that the SLM 18 can be operated in a threshold mode operation in which birefringence is selectively induced in the light modulation layer 34, dependently on an effective voltage (electric field) developed through the light modulation layer 34. The effective voltage is determined dependently on intensity of the write light image F2 incident in the photoconductive layer 35 and the AC bias voltage applied between the electrode films 31 and 30. In the SLM 18 of this example, when the AC bias voltage (voltage amplitude) is changed while the intensity of the write light incident on the photoconductive layer 35 is maintained to be fixed, birefringence is induced in the light modulation layer 34 when the AC bias voltage is lower than a predetermined threshold value. In contrast, when the AC bias voltage is greater than the predetermined threshold value, birefringence is not induced in the light modulation layer 34.

According to the present embodiment, therefore, the threshold value voltage controller 27 controls the SLM controller 26 to apply the AC bias voltage of such a value that may induce birefringence in the layer 34 at a region where the high intensity spectral component of the light image F2 is incident in the layer 35 while preventing the birefringence from being induced at a region where the low intensity spectral component of the light image F2 is incident in the layer 35. It is further noted that the amount of the AC vias voltage is such that the birefringence induced in the layer 35 due to the high intensity spectral component rotates the polarization plane of the read light incident in the layer 34 by 90 degrees. This bias voltage control therefore induces birefringence in the layer 34 only at regions where the high-intensity periodic circuit pattern of the image F2 is incident, the region being now indicated by a reference character F2' in FIG. 5.

The read light image F1 incident on the front surface of the substrate 32 of the SLM 18 travels through the light modulating layer 34, reflects off the reflecting layer 36, travels again through the light modulating layer 34, and outputs from the front surface of the substrate 32 of the SLM as an output light image F1'. While traveling through the light modulating layer 34, the light image F1 has its polarization plane rotated by 90 degrees at the region where the birefringence is induced. It is noted that the read light image F1 and the write light image F2 are in complete symmetry with respect to the reflective layer 36. Accordingly, the polarization plane of the high-intensity spectral component for the periodic circuit patterns of the image F1 is rotated by 90 degrees, while the polarization plane of the low-intensity spectral component for the random patterns of the defects and foreign matters is not rotated. Accordingly, the output light image F1' has a high intensity spectral component with its polarization plane rotated by 90 degrees and a low intensity spectral component with its polarization plane not rotated.

The half mirror 17 introduces the output image F1' to the analyzer 22, which blocks transmission of the component of the output image F1' with its polarization plane being rotated by 90 degrees. Accordingly, only the low intensity spectral component corresponding to the defects and foreign matters is guided to the Fourier transform lens 23 where the spectral component is subjected to inverse Fourier transformation into a real spatial image of the defects in and foreign matters on the objective 11. The real spatial image is then picked up by the pick up device 24 and is processed by the central controller 25.

As described above, the optical detector of the present embodiment can perform its detecting operation with the use of the single light source (laser source) 13. Therefore, the optical detector has a simple construction.

Because the read light image F1 and the write light image F2 are completely identical spectral patterns, it is possible to differentiate, by 90 degrees, the polarization plane of the spectral component corresponding to the random defects and foreign matters from the polarization plane of the spectral component corresponding to the periodic circuit pattern. It is therefore possible to ensurely extract or separate the low-intensity spectral component corresponding to the defects and foreign matters, from the mixture of the low-intensity spectral component with the high-intensity spectral component corresponding to the periodic circuit patterns. Accordingly, it is possible to provide a clean real image of the defects and foreign matters on the objective 11.

Additionally, after when the optical system in the optical detector is precisely positioned, it is unnecessary to adjust the optical system. The optical detection is therefore easily conducted and is improved in its accuracy.

When the intensities of the light images F1 and F2 vary in accordance with the change of the objective 11, the threshold value voltage controller 27 may change the AC bias voltage applied from the SLM controller 26 to the SLM 18, to thereby change writing sensitivity of the SLM 18. Thus, the SLM 18 can be always controlled to be operated in its threshold operation for various objectives. Accordingly, the optical detector of this embodiment can detect various objectives 11 with simply controlling the bias voltage applied to the SLM 18 in accordance with the objectives 11.

When the reflection type ferroelectric liquid crystal spatial light modulator (FLC-SLM) produced by HAMAMATSU PHOTONICS K. K. (trade name "FLC-SLM X4601") is employed as the SLM 18, the photoconductive layer 35, the reflective layer 36, and the liquid crystal layer 34 are made from hydrogenated amorphous silicon (α-Si:H), a dielectric mirror, and ferroelectric liquid crystal, respectively. The SLM controller 26 should apply the SLM 18 with the electric voltage of 10 [volts] as shown in FIG. 11 (b) to control the SLM 18 to achieve the threshold operation, in the case where the high-intensity spectral component and the low-intensity spectral component of the image F2 have intensities higher and lower than the predetermined threshold intensity Tl of FIG. 11 (a), respectively. It is noted the write light image F2 and the read light image F1 are simultaneously irradiated on the both sides of the SLM as indicated by dotted line in FIG. 11 (b).

An optical detector according to a second preferred embodiment of the present invention will be described below while referring to FIGS. 8 through 10. The second embodiment employs a transmission type optically-addressed SLM.

Figure 8:
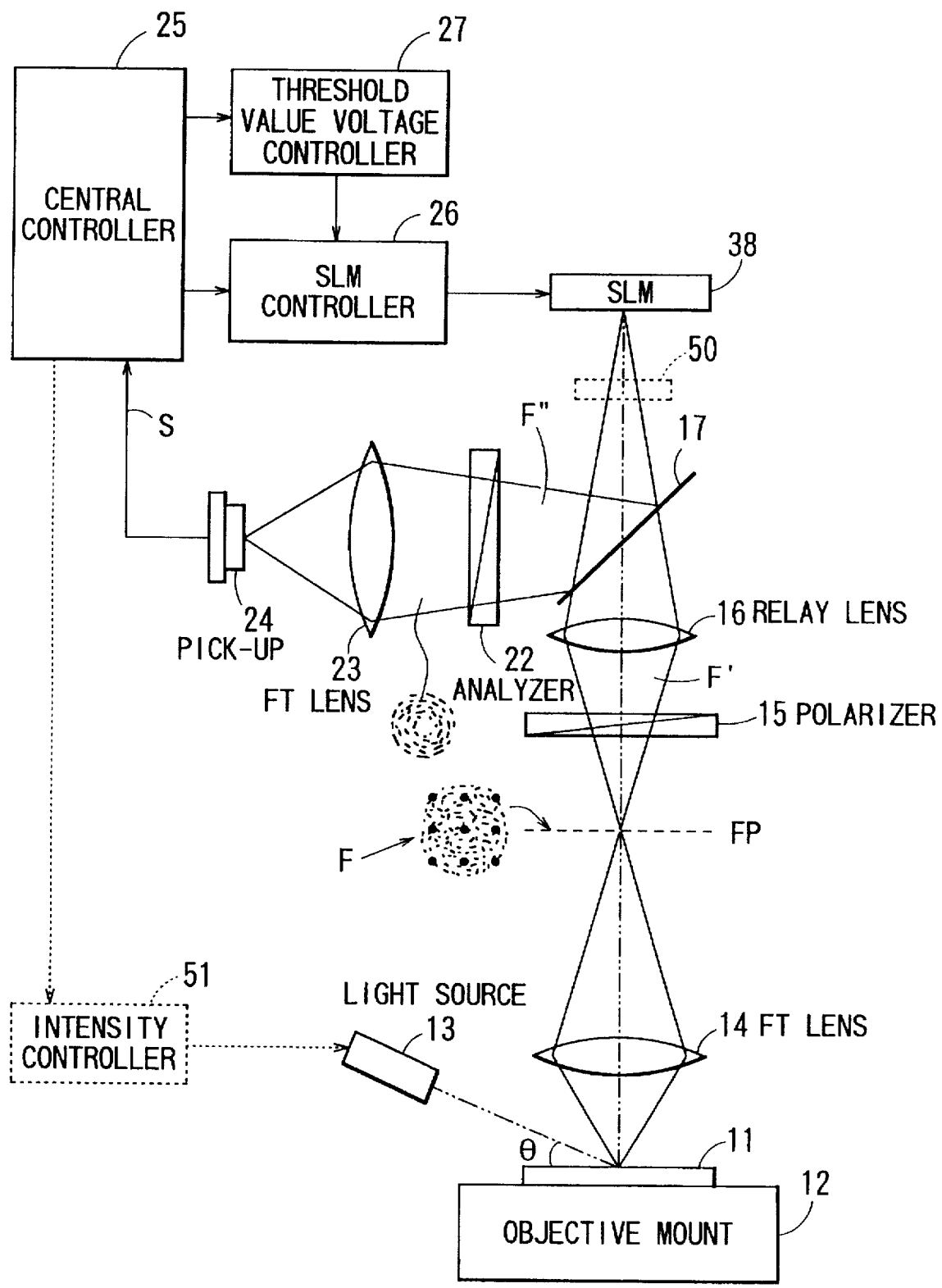
FIG. 8 illustrates an overall structure of an optical detector of a second preferred embodiment of the present invention.

A description of the overall structure of the optical detector will be first provided while referring to FIG. 8. Similarly to the optical detector of the first embodiment, the optical detector of this embodiment includes: an objective mount 12; a laser light source 13; a Fourier transform lens 14; a polarizer 15; a relay lens 16; a half mirror 17; an SLM 38; a analyzer 22; another Fourier transform lens 23 (inverse Fourier transform lens); a solid state image pick up device 24; a central controller 25; an SLM controller 26; and a threshold value controller 27 which are located in the same manner as in the optical detector of the first embodiment of FIG. 5. Accordingly, the optical detector of this embodiment is the same as that of the first embodiment except that the reflective mirrors 19–21 are omitted from the optical detector of this embodiment and that the SLM 38 employed in this embodiment is a transmission type optically-addressed SLM 38.

With the above-described structure, similarly as in the first embodiment, the Fourier transformed image F' having passed through the half mirror 17 is inputted in the SLM 38. As will be described later, the SLM 38 is controlled by a combination of the SLM controller 26 and the threshold voltage adjusting portion 27 to modulate only the high intensity spectral component of the Fourier transformed image F' by 90°, to produce a regionally modulated light image F''. The modulated light image F'' is outputted from the SLM 38 and reflected off the half mirror 17 so as to fall incident on a analyzer 22. The detector 22 is for blocking the 90° modulated polarized portion of the light image F''. Therefore, the unmodulated low intensity spectral component of the light image F'' is only transmitted through the analyzer 22 so as to be inverse Fourier transformed by the Fourier transform lens 23 to reproduce a real spatial image. The real spatial image is picked up by the solid-state image pick up device 24.

Figure 9:
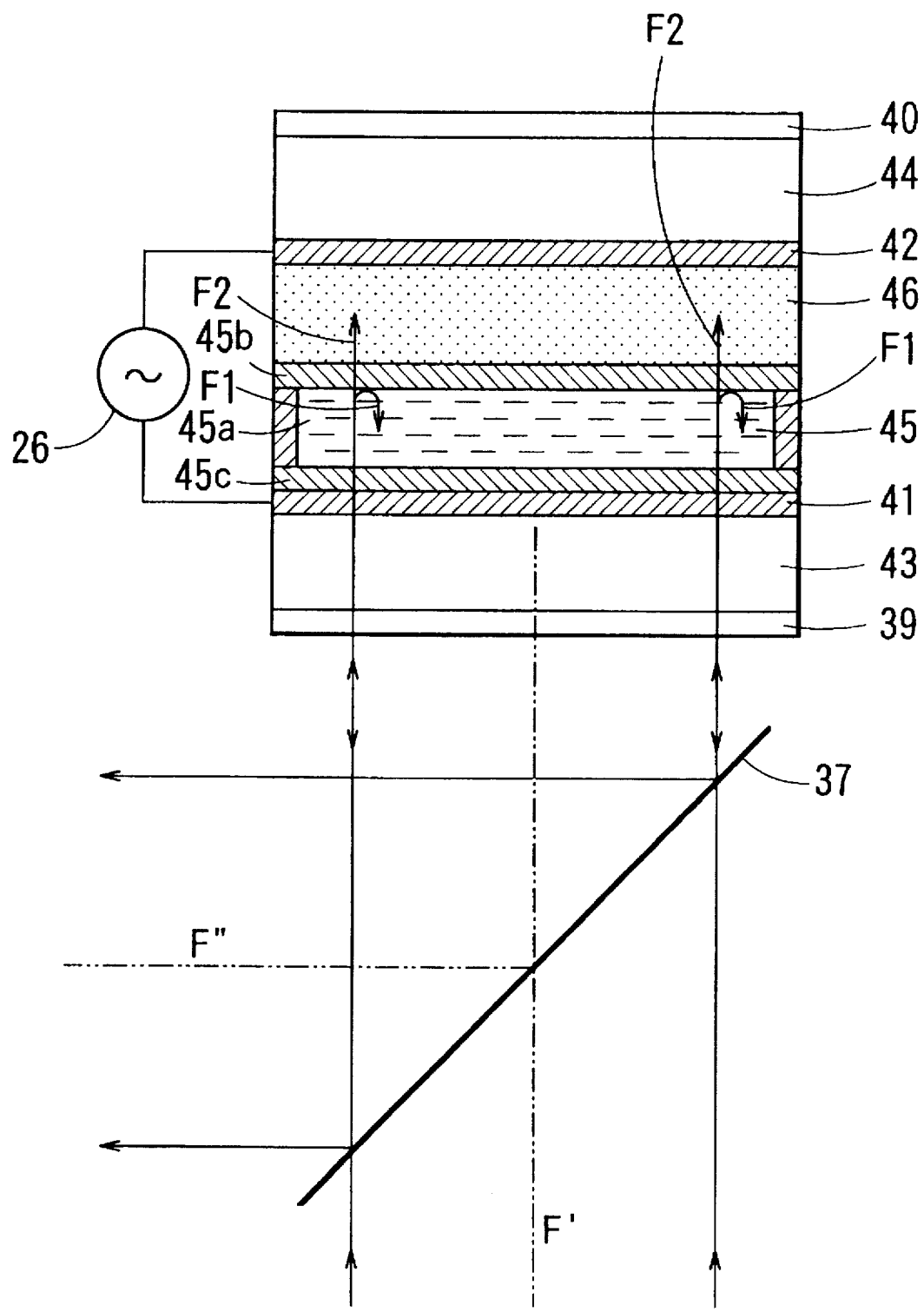
FIG. 9 illustrates a structure of a transmission type optically-addressed type SLM employed in the optical detector of FIG. 8.
Figure 10:
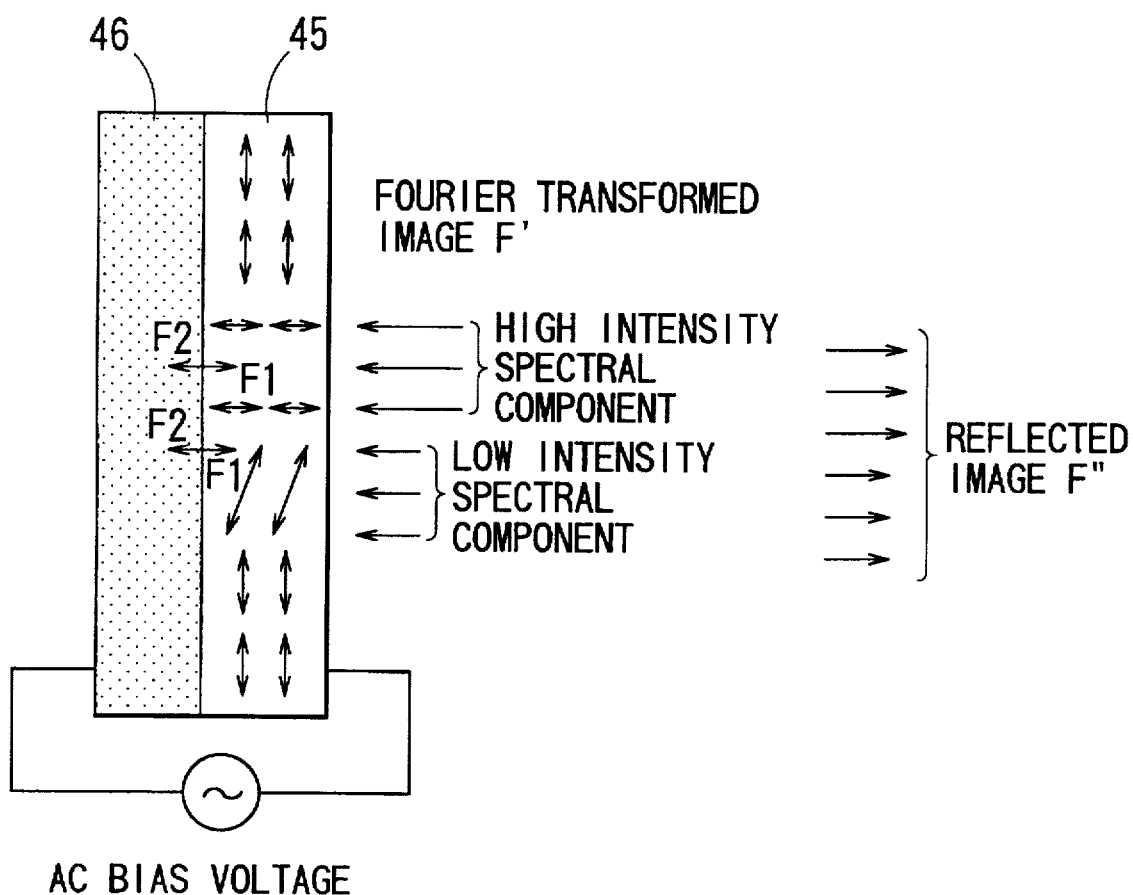
FIG. 10 illustrates an operation of the transmission type optically-addressed type SLM employed in the optical detector of FIG. 8.

Next, an explanation of the structure and function of the transmission type SLM 38 employed in the present embodiment will be provided while referring to FIGS. 9 and 10. The transmission type SLM 38 is the same as the reflection type SLM 18 of FIG. 6, except that the reflection layer 36 is omitted.

More specifically, as shown in FIG. 9, the SLM 38 includes a photoconductive layer 46 and a light modulation layer 45 sandwiched between a pair of confronting substrates 44 and 43. The light modulation layer 45 serves as a light modulating part, and is made from a light modulating material 45a such as twisted nematic (TN) liquid crystal or ferroelectric liquid crystal sandwiched between a pair of alignment layers 45b and 45c. The photoconductive layer 46 serves as an optically-addressing part, and is made from a photoconductive material such as amorphous silicon (α-Si). The confronting substrates 44 and 43 are made from transparent glass. The outward facing side of each confronting substrate 44 and 43 has coated thereon an AR coat layer 40 and 39 respectively. The inward facing side of each confronting substrate 44 and 43 has accumulated thereon a transparent electrode film 42 and 41 respectively. The SLM controller 26 in the form of a power source is provided with one terminal connected to the transparent electrode film 42 and the other terminal connected to the transparent electrode 41. The SLM controller 26 thereby applies an AC bias voltage between the pair of transparent electrode films 42 and 41.

The SLM 38 having the above-described structure is located such that the Fourier transformed light image F' having passed through the half mirror 17 falls incident on the front surface of the substrate 43 to travel through the substrate 43 and the light modulating layer 45. The light image F' then partly enters the photoconductive layer 46 and is partly reflected by the interface between the layers 46 and 45 due to difference between the refractive indices of the layers 46 and 45. It is noted that the refractive indices of the amorphous silicon and the nematic liquid crystal are 4 and 1.5, respectively. Accordingly, when the layers 46 and 45 are made from the amorphous silicon and the nematic liquid crystal, for example, about 45% of the total intensity of the light image F' is reflected, and about 55% of the total intensity of the light image F' travels into the layer 46. The reflected part of the light image F, is referred to as a "read light image F1," hereinafter, and the transmitted part of the light image F' is referred to as a "write light image F2," hereinafter. The read light image F1 and the write light image F2 therefore have identical patterns.

In the photoconductive layer 46 thus receiving the write light image F2, the electrical resistance changes in proportion to the intensity of each spectral portion of the write light image F2. The effective voltage developed in regions of the light modulation layer 45 therefore corresponds to the resistance value at corresponding regions of the photoconductive layer 46.

Also in this embodiment, the SLM 38 is operated in the threshold operation such that birefringence is selectively induced in the light modulation layer 45 dependently on the effective voltage developed through the light modulation layer 45. The effective voltage is determined dependently on both the spectral intensity of the write light image F2 and the AC bias voltage applied between the electrode films 42 and 41. For example, when the AC bias voltage (voltage amplitude) is changed while maintaining the intensity of write light incident to the photoconductive layer 46 to be fixed, birefringence is induced in the light modulation layer 45 when the AC bias voltage is lower than a predetermined threshold value. When the AC bias voltage is greater than the predetermined threshold value, birefringence is not induced in the light modulation layer 45.

Accordingly, similarly to the first embodiment, the threshold value controller 27 controls the SLM controller 26 to apply the AC bias voltage of such a value that may induce birefringence in the layer 45 at a region where the high intensity spectral component of the light image F2 is incident in the layer 46 while preventing the birefringence from being induced at a region where the low intensity spectral component of the light image F2 is incident in the layer 46. This bias voltage control therefore induces birefringence in the layer 45 only at regions where the high-intensity periodic circuit pattern of the image F2 is incident. It is further noted that the amount of the AC vias voltage is such that the birefringence induced in the layer 45 due to the high intensity spectral component rotates the polarization plane of the read light incident in the layer 45 by 90 degrees.

Accordingly, when the Fourier transformed image F' is continuously irradiated on the SLM 38, the read light image F1 continuously travelling through the light modulating layer 45, reflecting off the interface between the layers 45 and 46, and travelling again through the light modulating layer 45 outputs from the front surface of the SLM 38 as an output light image F". While traveling through the light modulating layer 45, the light image F1 has its polarization plane rotated by 90 degrees at the region where the birefringence is induced. It is noted that the read light image F1 and the write light image F2 are completely the same with each other. Accordingly, the polarization plane of the high-intensity spectral component of the periodic circuit pattern of the image F1 is rotated by 90 degrees, while the polarization plane of the low-intensity spectral component for the random pattern of the defects and foreign matters is not rotated. Accordingly, the output light image F" has a high intensity spectral component with its polarization plane rotated by 90 degrees and a low intensity spectral component with its polarization plane not rotated.

The half mirror 17 introduces the output image F'" to the analyzer 22, which blocks transmission of the component of the output image F1' with its polarization plane being rotated by 90 degrees. Accordingly, only the low intensity spectral component corresponding to the defects and foreign matters is guided to the Fourier transform lens 23 where the spectral component is subjected to inverse Fourier transformation into a real spatial image of the defects in and foreign matters on the objective 11. The real spatial image is then picked up by the pick up device 24 and is processed by the central controller 25.

As described above, the optical detector of the present embodiment can perform its detecting operation with the use of the single light source (laser source) 13. Therefore, the optical detector has a simple construction.

Especially in the present embodiment, the single optical image F' is simply introduced into one side of the SLM 38. Accordingly, it is possible to omit the optical elements for individually guiding the read light image and the write light image to individual sides of the SLM used in the first embodiment. Accordingly, the device has a simple structure and is more improved in its detection accuracy.

Additionally, after when the optical system in the optical detector is precisely adjusted, it is unnecessary to readjust the optical system. The optical detection is therefore simply attained and improved in its accuracy.

When the intensity of the light image F' varies in accordance with the change of the objective 11, the threshold value controller 27 may change the AC bias voltage applied from the SLM controller 26 to the SLM 38, to thereby change writing sensitivity of the SLM 38. Thus, the SLM 38 can be always controlled to be operated in the threshold mode for the various objectives 11. Accordingly, the optical detector of this embodiment can detect various objectives 11 with simply controlling the bias voltage applied to the SLM 18 in accordance with the objectives 11.

While the invention has been described in detail with reference to specific embodiments thereof, it would be apparent to those skilled in the art that various changes and modifications may be made therein without departing from the spirit of the invention, the scope of which is defined by the attached claims.

In each of the above-described embodiments, the AC bias voltage applied to the SLM is selected to a value that can rotate the polarization plane of the high-intensity spectral component by 90 degrees. However, the AC bias voltage can be selected to various values that can rotate the polarization plane by various degrees. The AC bias voltage may be selected to values that can selectively induce birefringence capable of differentiating the polarization planes of the high intense spectral component for the periodic circuit pattern and of the low intense spectral component for the random defect or foreign matter. In such a case, the polarizer 15 and the analyzer 22 should be selected to be suited for the birefringence induced in the SLM.

Because the SLMs can be generally operated in the threshold mode operation, various types of optically-addressed SLMs can be employed in the optical detector of the present invention. In other words, the material for the light modulating layers 34 and 45 of the SLMs 18 and 38 are not limited to the liquid crystal. The material may be selected from ceramics such as PLZT, organic material such as thermoplastics, inorganic crystal such as $LiNbO_3$ and DKDP, and the like. Another type of light modulating part may be used, in which a reflection path made from a $SiO_2$ paddle or a thin film is switched between ON state and OFF state so as to reflect or not to reflect the read light. Similarly, the material for the photoconductive layers 35 and 46 of the SLMs 18 and 38 are not limited to amorphous silicon. The material may be selected from CdS, BSO ($Bi_{12}SiO_{20}$), silicon photodiode, ZnS, GaAs, and the like.

In the above-described embodiments, the SLM controller 26 applies the SLM 18 (38) with an alternating current (AC) electric voltage. However, according to the kind of the SLM, the controller 26 may apply various types of voltages, such as direct current (DC) electric voltage, to the SLM.

In the first embodiment, an optical filter 50 may be located in the optical path for guiding the write light image F2 to the rear side of the SLM 18 constructed from the mirrors 19–21, as indicated by dotted line in FIG. 5. The optical filter controls the intensity of the write light image F2 incident on the photoconductive layer 35 to thereby adjust the writing sensitivity of the SLM 18. Thus controlling the intensity of the write light image F2 can also properly drive the SLM 18 in the threshold operation to selectively induce birefringence only at regions corresponding to the high intensity spectral component, even when the AC bias voltage applied to the SLM is not controlled.

Similarly, in the second embodiment, the filter 50 may be located in front of the SLM 38 for controlling the write light image F2, as indicated by dotted line in FIG. 8.

In place of the filter 50, an intensity controller 51 may be provided in each of the first and second embodiments, as indicated by dotted line in FIGS. 5 and 8. The intensity controller 51 is controlled by the central controller 25 to control the laser source 13 so as to adjust the intensity of the laser source irradiated on the objective 11. Thus controlling the intensity of the laser beam can also control the intensity of the write light image F2 to such a value that can properly drive the SLM in the threshold operation to selectively induce birefringence only at regions corresponding to the high intensity spectral component.

When the reflection type ferroelectric liquid crystal spatial light modulator (FLC-SLM) produced by HAMAMATSU PHOTONICS K. K. (trade name "FLC-SLM X4601") is employed as the SLM 18, when the SLM controller 26 applies the SLM 18 with the electric voltage of 10 [volts] as shown in FIG. 11 (b), the high-intensity spectral component and the low-intensity spectral component of the image F2 should be controlled to have intensities higher and lower than the predetermined threshold intensity TI of FIG. 11 (a), respectively.

According to the present invention, at least one of the intensity of the write light image F2 and the bias voltage may be controlled to adjust the write sensitivity of the SLM to ensure that the birefringence is induced only at regions where the high intensity spectral component for the periodic circuit pattern is incident.

What is claimed is:

1. An optical detector for detecting an abnormal portion in a periodic pattern in an objective, the optical detector comprising:

a light source for irradiating coherent light onto an objective;

a Fourier transform lens for receiving light diffracted and scattered at the objective and for Fourier transforming the light to generate a Fourier image, the Fourier image having a high intensity spectral component corresponding to the periodic pattern on the objective and a low intensity spectral component corresponding to the abnormal portion;

a polarizer for transmitting a predetermined polarization component of the Fourier image;

an optically-addressed spatial light modulator having an optically-addressing part and a light modulating part, the optically-addressing part and the light modulating part respectively receiving a write part and a read part of the predetermined polarization component of the Fourier image transmitted through the polarizer, at corresponding portions thereof;

threshold driving control means for controlling the spatial light modulator in its threshold operation so as to induce birefringence in the light modulating part at a region corresponding to an area in the optically-addressing part where the high intensity spectral component of the write part is incident while preventing birefringence from being induced in the light modulating part at a region corresponding to an area in the optically-addressing part where the low intensity spectral component of the write part is incident, the induced birefringence rotating the polarization plane of the high intensity spectral component of the read part incident in the light modulating part;

a analyzer for receiving the read part of the Fourier image outputted from the light modulating part of the optically-addressed type spatial light modulator and for blocking the high intensity spectral component thereof with its polarization plane having been rotated; and another Fourier transform lens for inverse Fourier transforming the low intensity spectral component into an real spatial image of the abnormal portion on the objective.

2. An optical detector of claim 1, wherein the spatial light modulator further includes a pair of electrodes for applying electric voltage through the optically-addressing part and the light modulating part, and wherein the threshold driving control means includes a voltage controlling means for controlling the electric voltage applied between the pair of electrodes to a value that induces birefringence in the light modulating part at a region corresponding to an area in the optically-addressing part where the high intensity spectral component is incident while preventing birefringence from being induced in the light modulating part at a region corresponding to an area in the optically-addressing part where the low intensity spectral component is incident.

3. An optical detector of claim 1, wherein the threshold driving control means includes intensity control means for controlling the intensities of the high intensity spectral component and the low intensity spectral component of the write part of the Fourier image to such values that induce birefringence in the light modulating part at a region corresponding to an area in the optically-addressing part where the high intensity spectral component is incident while preventing birefringence from being induced in the light modulating part at a region corresponding to an area in the optically-addressing part where the low intensity spectral component is incident.

4. An optical detector of claim 1, wherein the spatial light modulator further includes a reflective layer located between the optically-addressing part and the light modulating part for reflecting off the read part of the Fourier image travelled through the light modulating part.

5. An optical detector of claim 4, further comprising optical guiding means for guiding the write part of the Fourier image to the optically-addressing part and for guiding the read part of the Fourier image to the light modulating part do that the write part of the Fourier image and the read part of the Fourier image are received in the optically-addressing part and the light modulating part, respectively, substantially in symmetry with respect to the reflective layer.

6. An optical detector of claim 5, further comprising a filter for controlling intensity of the write part of the Fourier image guided by the optical guiding means to the optically-addressing part.

7. An optical detector of claim 1, wherein the spatial light modulator includes the light modulating part and the optically-addressing part contacted with each other by an interface defined therebetween, the light modulating part and the optically-addressing part having refractive indices different from each other, the spatial light modulator receiving the Fourier image transmitted through the polarizer to be incident on the light modulating part, the write part of the Fourier image passing through the interface to enter the optically-addressing part and the remaining read part of the Fourier image being reflected at the interface due to the difference in the refractive indices of the optically-addressing part and the light modulating part.

8. An optical detector of claim 1, wherein the optically-addressing part and the light modulating part of the spatial light modulator are a photoconductive layer and a liquid crystal layer, respectively.

9. An optical detector for detecting an abnormal portion in a periodic pattern in an objective, the optical detector comprising:

a light source for irradiating coherent light onto an objective;

a Fourier transform lens for receiving light diffracted and scattered at the objective and for Fourier transforming the light to generate a Fourier image, the Fourier image having a high intensity spectral component corresponding to the periodic pattern on the objective and a low intensity spectral component corresponding to the abnormal portion;

an optically-addressed spatial light modulator having a optically-addressing part and a light modulating part, each of the optically-addressing part and the light modulating part receiving the Fourier image at the corresponding portions;

threshold driving control means for controlling the spatial light modulator in its threshold operation so as to change a state in the light modulating part at a region corresponding to an area in the optically-addressing part where the high intensity spectral component of the Fourier image is incident while preventing the state from being changed in the light modulating part at a region corresponding to an area in the optically-addressing part where the low intensity spectral component of the Fourier image is incident, the changed state in the light modulating part modulating the high intensity spectral component of the Fourier image incident in the light modulating part;

separating means for receiving the Fourier image outputted from the light modulating part of the optically-addressed type spatial light modulator and for separating the modulated high intensity spectral component from the unmodulated low intensity spectral component; and another Fourier transform lens for inverse Fourier transforming the low intensity spectral component into a real spatial image of the abnormal portion on the objective.

* * * * *